United States Patent [19]

Rozzell, Jr.

[11] Patent Number: 5,885,767
[45] Date of Patent: Mar. 23, 1999

[54] METHODS AND COMPOSITIONS FOR QUANTITATING L-HOMOCYSTEINE AND/ OR L-METHIONINE IN A SOLUTION

[75] Inventor: J. David Rozzell, Jr., Burbank, Calif.

[73] Assignee: BioCatalytics, Inc., Burbank, Calif.

[21] Appl. No.: 83,459

[22] Filed: May 22, 1998

[51] Int. Cl.$^6$ .............................. C12Q 1/00; C12Q 1/48; C12Q 1/37; C12Q 1/54
[52] U.S. Cl. ................................ 435/4; 435/15; 435/23; 435/26; 435/14
[58] Field of Search .................................. 435/4, 15, 23, 435/26, 14

[56] References Cited

U.S. PATENT DOCUMENTS

| | | | |
|---|---|---|---|
| 5,478,729 | 12/1995 | Van Atta et al. ...................... | 435/7.93 |
| 5,631,127 | 5/1997 | Sundrehagen ............................... | 435/4 |
| 5,690,929 | 11/1997 | Lishko et al. ........................... | 424/94.5 |
| 5,715,835 | 2/1998 | Lishko et al. ........................... | 128/898 |

OTHER PUBLICATIONS

Ito et al; J. Biochem., vol. 79, pp. 1263–1272, (1976).
Esaki et al; Methods in Enzymology, vol. 143, pp. 291–297, (1983).
Chace, D.H. et al., "Rapid Diagnosis of Homocystinuria and Other Hypermethioninemias from Newborns' Blood Spots by Tandem Mass Spectrometry," *Clinical Chemistry* 42:3, 349–355 (1996).
N. Esaki and K. Soda, "L–Methionine γ–Lyase," *Biocatalytic Production of Amino Acids and Derivatives*, D. Rozzell and F. Wagner, editors, Hanser Publishers, Munich (1992), pp. 263–267.
Mudd SH, Levy HL, Skovby F., "Disorders of Transsulfuration," in Scriver CR, Beaudet AL, Sly WS, Valle D, eds., *The Metabolic and Molecular Basis of Inherited Disease*, McGraw–Hill Co., New York, 7th edition, 1995, Chapter 35, pp. 1279–1327.
Nakayama, T. et al., "Purification of Bacterial L–Methionine γ–Lyase," *Anal. Biochem.*, 138:421–424 (1984).
Passoneau and Lowry, "Fluorometer Direct Assay 0.1–8 nmol/mL," in *Enzymatic Analysis, A Practical Guide*, pp. 220–222, (1993).
Refsum, H., Helland, S. and Ueland, P.E., "Radioenzymic Determination of Homocysteine in Plasma and Urine," *Clinical Chemistry* 31:4, 624–628 (1985).
Sharpe, M. Elisabeth et al., "Methanethiol Production by Coryneform Bacteria: Strains from Dairy and Human Skin Sources and *Brevibacterium linens*,"*J. Gen Microbiol.* 101:345–349 (1977).
1988 Sigma Catalog, "Alphabetical List of Compounds," pp. 659–661.
1998 Sigma Catalog, "Diagnostic Kits and Reagents," p. 2629.
Sweetman, L., "Newborn Screening by Tandem Mass Spectrometry (MS–MS)," *Clinical Chemistry* 42:3, 345–346 (1996).
Tanaka, H. et al., "Properties of L–Methionine γ–Lyase from *Pseudomonas ovalis*," *Biochemistry*, 16:100–106 (1977).
Tanaka, et al., "Purification and Properties of Methioninase From *Pseudomonas ovalis*," *FEBS Letters*66:2307–2311 (1976).
Ueland, P.E. et al., "Total Homocysteine in Plasma or Serum: Methods and Clinical Applications," *Clinical Chemistry* 39:3, 1764–1779 (1993).

*Primary Examiner*—Louise N. Leary
*Attorney, Agent, or Firm*—Christie, Parker & Hale, LLP

[57] ABSTRACT

A method for quantitating L-homocysteine and/or L-methionine in a solution involves contacting a solution containing L-homocysteine and/or L-methionine with a reagent comprising methionine gamma-lyase and a cofactor capable of forming a Schiff base with the L-methionine and/or L-homocysteine for a time sufficient to catalyze the conversion of L-homocysteine and/or L-methionine to 2-ketobutyrate. The amount of 2-ketobutyrate formed is determined, and the amount of L-homocysteine and/or L-methionine present in the original solution can be determined based on the amount of 2-ketobutyrate formed. A composition for measuring the amount of L-homocysteine and/or L-methionine in a solution comprises methionine gamma-lyase, a cofactor capable of forming a Schiff base with the L-methionine and/or L-homocysteine and at least one 2-ketobutyrate detecting agent, but is substantially free of L-methionine, L-homocysteine, 2-ketobutyrate, pyruvate and mercury.

47 Claims, No Drawings

METHODS AND COMPOSITIONS FOR QUANTITATING L-HOMOCYSTEINE AND/OR L-METHIONINE IN A SOLUTION

FIELD OF THE INVENTION

This invention relates to methods and compositions for determining the concentration of L-homocysteine and/or L-methionine in a solution.

BACKGROUND AND DESCRIPTION OF THE PRIOR ART

L-Homocysteine is a naturally occurring amino acid that functions as a biosynthetic precursor to L-methionine. Applications of homocysteine have been proposed in the treatment of cancer and other serious disorders, increasing its importance as a pharmaceutical or as a pharmaceutical ingredient. Recently, elevated levels of L-homocysteine have also been correlated with the development of coronary artery disease. See Clarke et al, *New England Journal of Medicine*, 324: 1149–1155 (1991). As a result, many physicians now recommend diets and nutritional supplements to reduce L-homocysteine levels in blood. L-Methionine is an essential amino acid for animals; the racemic form of methionine commands a market of approximately 500 million dollars annually as an additive to animal feed.

The accurate quantitation of L-homocysteine and L-methionine is currently a challenge for analytical laboratories, particularly those analyzing samples of biological fluids. Given the nutritional and medical importance of these amino acids, accurate measurement of their concentrations is often necessary.

Quantitation of both L-homocysteine and L-methionine is especially important in the diagnosis and treatment of homocystinuria. Homocystinuria is a serious genetic metabolic disorder caused most commonly by a block in the pathway of methionine metabolism due to a deficiency of the enzyme cystathionine synthetase. The result is an accumulation of elevated levels of L-homocysteine, L-methionine and metabolites of L-homocysteine in the blood and urine. Homocystinuria is more fully-described in Mudd S H, Levy H L, Skovby F: Disorders of Transsulfuration, in Scriver C R, Beaudet A L, Sly W S, Valle D, eds., The Metabolic and Molecular Basis of Inherited Disease, McGraw-Hill Co., New York, 7th edition, 1995, pp. 1279–1327, the disclosure of which is hereby incorporated by reference.

The ability to detect both L-homocysteine and L-methionine is important in early screening for this disease. Classic homocystinuria, caused by a block in methionine metabolism due to cystathionine synthetase deficiency, is diagnosed by elevated L-methionine and L-homocysteine in blood and urine. In healthy patients, L-methionine and L-homocysteine are generally found in only trace amounts. In patients with classic homocysteinuria, L-methionine levels in the blood are generally above 67 $\mu$mol/L, and often above 134 $\mu$mol/L, and total L-homocysteine levels in the blood are as high as 500 $\mu$mol/L. See Ueland et al., Clinical Chemistry 39: 1764–1779 (1993); and Chace et al., Clinical Chemistry 42: 349–355 (1996), the disclosures of which are incorporated herein by reference. However, variant forms of homocystinuria are caused by lowered N-5-methyltetrahydrofolate homocysteine methyltransferase activity due to vitamin B12 deficiency and decreased N-5,10 methylene tetrahydrofolate reductase activity. These variant forms of homocystinuria are characterized by elevated L-homocysteine and normal or low blood levels L-methionine. Thus, an assay that detects only L-methionine, such as Guthrie microbiological assay that is currently used, can frequently produce false negative results, resulting in mis-diagnosis or delayed diagnosis and treatment.

Such failures or delays have serious, and often fatal, consequences. If untreated, death within the first year of life from homocystinuria is common. Because of the severity of the disease, 21 states currently mandate routine screening of all newborn babies for homocystinuria. The availability of a more reliable test could increase the accuracy in detecting this serious disorder and further broaden use of the test in neonatal screening.

Existing methodology for measuring L-homocysteine and/or L-methionine is poor. Currently, all neonatal screening assays for homocystinuria rely upon the Guthrie microbiological assay. Bacteria which require methionine for growth are cultured from blood specimens taken from the heel of newborn babies. The presence of L-methionine in the sample allows the growth of bacteria on an agar plate, and the diameter of the bacterial growth spot is measured. However, this test is not quantitative, and requires at least 1–2 days for a result. The Guthrie method also produces a high frequency of both false negatives and false positives. See Clinical Chemistry 42: 3, 349–355 (1996), the disclosure of which is hereby incorporated by reference. It is further limited by the fact that it cannot detect L-homocysteine at all. Since homocystinuria is frequently characterized by high levels of L-homocysteine, or its oxidized dimer homocystine, in the absence of high concentrations of L-methionine, the current test is far less reliable than is desired. Furthermore, the existing Guthrie assay does not lend itself to rapid testing for daily management of the levels of L-homocysteine and/or L-methionine, an important aspect of controlling the effects of the disease through diet. A convenient assay with greater reliability would provide significantly improved information to the neonatal physicians, permitting more timely diagnosis and more effective treatment of homocystinuria. Such an assay could also be used by patients and their doctors for daily monitoring of blood or urine levels of L-homocysteine and/or L-methionine, improving daily management of the disease through diet and medications and for other assays of L-homocysteine, L-homocystine (which may be easily reduced to L-homocysteine), and L-methionine.

An assay for L-homocysteine is described in U.S. Pat. No. 5,631,127, which relates to a method for assaying L-homocysteine in a blood, plasma, or urine sample. The method described in this patent comprises the steps of reacting homocysteine with a homocysteine-converting enzyme that also requires at least one substrate other than homocysteine, and without chromatographic separation, assessing a non-labeled analyte selected from a homocysteine co-substrate and the homocysteine conversion products. The example given in this patent is the enzyme S-adenosylhomocysteine hydrolase, and the analyte is adenosine. As adenosine reacts with L-homocysteine to form S-adenosylhomocysteine, the amount of L-homocysteine may be determined by measuring the amount of adenosine consumed, and correlating this with the amount consumed in a set of standard solutions of L-homocysteine. Typically, the change in adenosine concentration is accomplished by immunoassay.

A direct immunoassay for homocysteine is described in U.S. Pat. No. 5,478,729. The method of U.S. Pat. No. 5,478,729 requires chemical modification of the homocysteine to increase its immunogenicity. Antibodies that are specific to the modified homocysteine are prepared, and the modified homocysteine is detected immunologically. This assay is useful in detecting L-homocysteine in the presence of L-cysteine, but the various steps involved in chemical modification and immunological detection, as well as the need for an antibody which is not readily available, make it inconvenient to carry out. Neither of these assays is readily adaptable to doctor's office or home use.

Other assays for detecting L-homocysteine and/or L-methionine are possible, but all have drawbacks. Tandem mass spectrometry on dried blood spots has recently been proposed; this method provides accurate data, but requires very expensive equipment, expensive isotopically-labeled compounds, and highly skilled operators to carry out. Because of its very high cost, this method is probably better suited for confirmation of a preliminary diagnosis made on the basis of a less expensive screening assay. As an alternative, urine or blood samples can be prepared for amino acid chromatography, and L-homocysteine and/or L-methionine is then measured by high performance liquid chromatography (HPLC). Fiskerstrand et al. describe a method of L-homocysteine assay involving fluorescent labeling of serum thiols, followed by HPLC separation and detection of the L-homocysteine derivative from the various other sulfur-containing compounds. See Clin. Chem. 39, 2630271 (1993), the disclosure of which is incorporated herein by reference. However, these methods are time consuming, costly, and not readily available to many laboratories. The cyanide-nitroprusside test may be used to detect homocysteine, but it is non-selective, producing a color change from a non-specific reaction with all sulfhydryl compounds in urine and blood, including cysteine, peptides, proteins, and metabolites. The cyanide-nitroprusside test also gives no reaction at all with L-methionine, and would give false negative results for all homocystinurics producing only symptoms of hypermethionemia. Further, this test is well known to give false positive results on urine for people with cystinuria and acetonuria. See Khashayer Sakhaee and Roger A. L. Sutton, Kidney Stones: Medical and Surgical Management Chapter 46, F. L. Coe et al eds., Lippencott-Raven Publishers, Philadelphia, Pa. (1996), the disclosure of which is hereby incorporated by reference.

Thus, the existing assays for determining the concentration of L-homocysteine and/or L-methionine in biological fluids do not provide the desired selectivity and speed, and frequently give false positive and false negative results. A more quantitative assay that can selectively and rapidly measure the L-homocysteine and/or L-methionine concentration in a biological sample such as urine or blood, without false positive results caused by other sulfhydryl compounds present and without false negative results due to limited sensitivity, would facilitate screening of all newborns for homocystinuria. Further, the assay would be useful in research with homocysteine as an anti-cancer drug, in monitoring L-homocysteine levels in persons at risk for coronary artery disease, and in assessing L-methionine concentrations in pharmaceutical mixtures and nutritional products such as animal feed. Availability of such an assay for these purposes, as well as for the determination of the concentrations of L-homocysteine and/or L-methionine in any other solution, would be greatly desired.

SUMMARY OF THE INVENTION

The present invention discloses a quantitative, selective enzymatic assay for determining the levels of L-homocysteine and/or L-methionine in solution. Such solutions include laboratory mixtures, urine, and other biological fluids. As a clinical diagnostic assay, the present invention can provide physicians with rapid, more accurate knowledge of the actual concentrations of L-homocysteine and/or L-methionine, permitting more rapid and accurate diagnosis of the condition of homocystinuria. Furthermore, the simplicity and rapidity of the assay permits immediate feedback to physicians and to patients doing home monitoring. The assay may also be used for detection of L-homocysteine and/or L-methionine in foods, beverages, and other products.

In one embodiment, the present invention is directed to a method for measuring the amount of L-homocysteine and/or L-methionine in a solution comprising the steps of:

(a) contacting the solution containing L-homocysteine and/or L-methionine with a reagent comprising methionine gamma-lyase, or a derivative thereof, and a cofactor capable of forming a Schiff base with the L-methionine and/or L-homocysteine, for a time sufficient to catalyze the reaction of L-homocysteine and/or L-methionine to form 2-ketobutyrate;

(b) determining the amount of 2-ketobutyrate formed; and (c) determining the amount of L-homocysteine and/or L-methionine in the original solution based on the amount of 2-ketobutyrate formed.

More particularly, the present invention is directed to a method for measuring the amount of L-homocysteine and/or L-methionine a biological sample such as urine or blood using the method steps described above. In a further embodiment, the present invention is directed to a method for diagnosing homocystinuria by detecting or quantitating L-homocysteine and/or L-methionine in a biological sample such as urine or blood.

Each mole of L-homocysteine and/or L-methionine reacted with L-methionine gamma-lyase, or a derivative thereof, forms one mole of 2-ketobutyrate. Therefore, when reacted to substantial completion, the number of moles of 2-ketobutyrate formed is approximately equal to the number of moles of L-homocysteine and/or L-methionine in the original solution. Preferably, the solution containing L-homocysteine and/or L-methionine is contacted with the reagent for a time sufficient to catalyze the conversion of L-homocysteine and/or L-methionine to 2-ketobutyrate to substantial completion.

The amount of 2-ketobutyrate formed can be determined in several ways. For example, the amount of 2-ketobutyrate formed can be determined by oxidizing NADH (reduced nicotinamide cofactor) or a derivative thereof, to NAD+, or a derivative thereof, in the presence of the enzyme lactic dehydrogenase and determining the amount of NAD+ formed. The amount of NAD+ formed can be determined by measuring the decrease in absorbance at 340 nm and correlating the change in absorbance to the amount of NADH oxidized to NAD+ using Beer's Law and the known extinction coefficient of NADH. Alternatively, the amount of NAD+ can be determined by reacting it with a dye capable of undergoing a color change when oxidized. Alternatively, the amount of 2-ketobutyrate formed can be determined by reacting the 2-ketobutyrate with a reagent comprising a hydrazine such as 2,4-dinitrophenylhydrazine to form 2-ketobutyryl 2,4-dinitrophenylhydrazone and measuring the amount of 2-ketobutyryl 2,4-dinitrophenylhydrazone formed.

In another embodiment, the invention is directed to a method for the colorimetric detection of L-homocysteine and/or L-methionine in a solution comprising the steps of:

(i) contacting a sample containing L-homocysteine and/or L-methionine with a solution, mixture, or support material comprising NADH, or a derivative thereof, lactic dehydrogenase, or a derivative thereof, methionine gamma-lyase, or a derivative thereof, a cofactor capable of forming a Schiff base with the L-methionine and/or L-homocysteine, and a dye capable of producing a color-change when oxidized; and (ii) determining the amount of L-homocysteine and/or L-methionine present based on the relative intensity of the observed color.

In another embodiment of the invention, there is provided a composition for measuring the amount of L-homocysteine and/or L-methionine in a test sample. The composition comprises L-methionine gamma-lyase, or a derivative thereof, a cofactor capable of forming a Schiff base with the L-methionine and/or L-homocysteine, and at least one 2-ketobutyrate detecting agent, and is substantially free of both L-homocysteine and L-methionine. It is undesirable to include L-homocysteine and L-methionine in the composition, as they would react with the methionine gamma-lyase to form 2-ketobutyrate, prohibiting a determination of the amount of L-homocysteine and/or L-methionine in the test solution. Preferably, the composition is also substantially free of 2-ketobutyrate, pyruvate, and mercury. It is undesirable to include pyruvate and 2-ketobutyrate in the composition, as they would react with the 2-ketobutyrate detecting agent. Mercury can cause interference by reacting with thiol groups present in the enzyme or homocysteine. As used herein, the term "substantially free" means less than about 5%, preferably less than about 1%, and still more preferably less than about 0.5%, by weight, based on the total weight of the composition. In another embodiment, the composition further comprises a thiol reducing agent. The composition can be in the form of a solution or mixture or associated with a support material.

In another embodiment, the invention is directed to a method for measuring the amount of L-homocysteine and the amount of L-methionine in a solution containing both L-homocysteine and L-methionine. The solution is treated with an oxidizing agent in a manner sufficient to oxidize substantially all of the L-homocysteine to a disulfide or mixed disulfide. The solution is then contacted with a reagent comprising methionine gamma-lyase, or a derivative thereof, and a cofactor capable of forming a Schiff base with the L-methionine and/or L-homocysteine, for a time sufficient to catalyze the reaction of L-methionine to form 2-ketobutyrate. The amount of 2-ketobutyrate formed is determined, and the amount of L-methionine in the original solution can be ascertained based on the amount of 2-ketobutyrate formed. The solution is then treated with a reducing agent in a manner sufficient to reduce substantially all L-homocystine and mixed disulfides containing half homocystine present in the sample to produce L-homocysteine. The solution is then contacted with a reagent comprising methionine gamma-lyase, or a derivative thereof, and a cofactor capable of forming a Schiff base with the L-methionine and/or L-homocysteine, for a time sufficient to catalyze the reaction of L-homocysteine to form 2-ketobutyrate. The amount of 2-ketobutyrate formed is determined, and the amount of L-homocysteine in the original solution is ascertained based on the amount of 2-ketobutyrate formed.

In another embodiment, the invention is directed to a method for diagnosing homocystinuria comprising determining the amount of L-homocysteine and/or L-methionine in a biological fluid as described above. The amount of L-homocysteine and/or L-methionine is then correlated to that known to be indicative of homocysteinuria.

DETAILED DESCRIPTION OF THE INVENTION

The present invention is directed to methods and compositions for measuring the amount of L-homocysteine and/or L-methionine in a solution. In one embodiment, the invention is directed to a method for detecting the amount of L-homocysteine and/or L-methionine in a solution comprising:

(a) contacting a solution containing L-homocysteine and/or L-methionine with a reagent comprising L-methionine gamma-lyase, or a derivative thereof, and a cofactor capable of forming a Schiff base with the L-methionine and/or L-homocysteine, for a time sufficient to catalyze the reaction of L-homocysteine and/or L-methionine to form 2-ketobutyrate;

(b) determining the amount of 2-ketobutyrate formed; and (c) determining the amount of L-homocysteine and/or L-methionine in the original solution based on the amount of 2-ketobutyrate formed.

Central to this invention is the use of the enzyme methionine gamma-lyase (also known as methionase, E.C. 4.4.1.11), an enzyme involved in methionine metabolism. It catalyzes the conversion of L-methionine to form methanethiol, 2-ketobutyrate, and ammonia. The enzyme is widely distributed in pseudomonads and other bacteria. The natural biosynthetic reaction catalyzed by the enzyme is as follows:

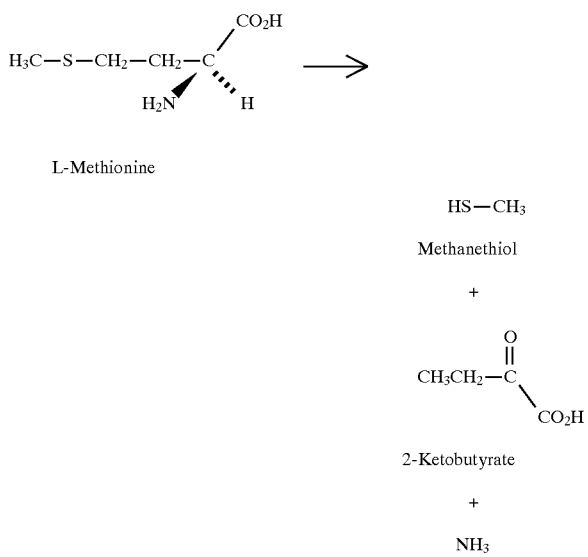

While the "normal" function of methionine gamma-lyase is the reaction shown above, it also catalyzes the conversion of L-homocysteine into 2-ketobutyrate, ammonia, and bisulfide. See N. Esaki and K. Soda, in "Biocatalytic Production of Amino Acids and Derivatives," D. Rozzell and F. Wagner, editors, Hanser Publishers, Munich (1992), pp. 263–267 the disclosure of which is incorporated herein by reference. The reaction catalyzed by methionine gamma-lyase on L-homocysteine is shown below.

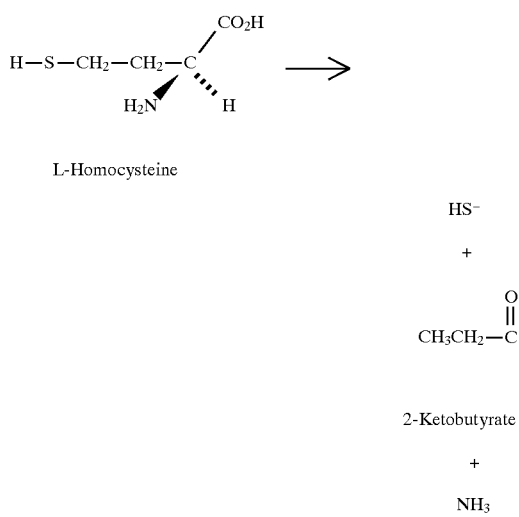

L-Homocysteine

2-Ketobutyrate

+

NH₃

The present invention exploits both the "natural" and the "unnatural" activities of methionine gamma-lyase for the detection and quantitation of L-homocysteine and/or L-methionine.

Kinetic measurements of the rates of conversion of both L-homocysteine and L-methionine with methionine gamma-lyase from *Pseudomonas putida* ICR 3460 demonstrate that both compounds are excellent substrates, as reported by Nakayama et al. in Anal. Biochem., 138: 421 (1984), the disclosure of which is incorporated herein by reference. The Vmax for L-methionine as a substrate for methionine gamma-lyase is about 20 micromoles per minute per milligram of pure protein; the Vmax for L-homocysteine as a substrate for methionine gamma-lyase is 36 micromoles per minute per milligram of pure protein. As recognized by those skilled in the art, the Vmax is the maximum velocity of the enzyme at saturating substrate concentrations.

Importantly, methionine gamma-lyase has low activity on L-cysteine (formed by reduction of the disulfide bond in L-cystine) and other amino acids which can react via a beta or gamma elimination mechanism similar to that for L-methionine and L-homocysteine, as reported by Nakayama et al. in Anal. Biochem., 138: 421 (1984), the disclosure of which is incorporated herein by reference. L-Threonine, L-tryptophan, L-serine, L-tyrosine, and L-homoserine all are either very poor substrates or do not react at all with the enzyme. Nor do these amino acids inhibit methionine gamma-lyase appreciably at concentrations between 0.1 mM and 10 mM. This is especially relevant to the use of methionine gamma-lyase for the quantitation of L-homocysteine and/or L-methionine in solutions of urine, blood, and other samples of biological origin where other amino acids are often present. Thiol compounds such as β-mercaptoethanol, dithiothreitol, dithioerythritol, thioacetic acid and salts thereof, and the like are also not acted on by the enzyme nor do they inhibit the enzyme. The high selectivity of methionine gamma-lyase for L-homocysteine and/or L-methionine relative to other naturally-occurring amino acids permits the accurate quantitation of L-homocysteine and/or L-methionine in solution, particularly solutions of biological origin such as urine and blood samples, with few side reactions that might produce false positive signals or interference.

As explained above, the enzyme methionine gamma-lyase converts L-methionine into methanethiol, ammonia, and 2-ketobutyrate and converts L-homocysteine into bisulfide, ammonia, and 2-ketobutyrate. The equilibrium constant for the reaction of methionine gamma-lyase with either substrate is very high, favoring the products. Therefore, if given sufficient time, this reaction proceeds essentially to completion in the presence of a catalytic amount of methionine gamma-lyase to produce 1 mole of 2-ketobutyrate per mole of L-homocysteine and/or L-methionine present. Preferably, the concentration of methionine gamma-lyase, or derivative thereof, in the reagent ranges from about 0.005 mg/ml to about 5 mg/ml. Depending on the concentration of methionine gamma-lyase in the reagent, the time required for substantial completion, i.e., at least about 90% conversion, of the reaction of L-homocysteine and/or L-methionine to form 2-ketobutyrate may take up to about 30 minutes or more, but is preferably less than about 1 minute.

Derivatives of methionine gamma-lyase may also be used in the practice of this invention. As used herein, the term derivatives, with respect to enzymes, refers to mutants produced by amino acid deletion, replacement, or modification; mutants produced by recombination and/or DNA shuffling; and salts, solvates, and other chemically modified forms that retain enzyme activity. A method for creating a derivative of methionine gamma-lyase by DNA shuffling useful in the present invention is described in U.S. Pat. No. 5,605,793, the disclosure of which is incorporated herein by reference.

The presence of a cofactor capable of forming a Schiff base with the substrate, i.e., L-methionine and/or L-homocysteine, is required for full activity of the enzyme methionine gamma-lyase. The most common cofactor used by methionine gamma lyase is pyridoxal phosphate, although other cofactors are possible, including enzyme-bound 2-ketoacids such as pyruvate. During recovery and purification of the enzyme, pyridoxal phosphate, or a derivative thereof, is commonly added to the buffers and solutions that contain the enzyme, so that preparations of methionine gamma-lyase, including solutions, precipitates, lyophilized protein, and crystallized enzyme, often contain pyridoxal phosphate. Additional amounts of pyridoxal phosphate, or other cofactor, may be added to the reagents or the preparations of methionine gamma-lyase used in the practice of this invention, if desired. When added to the reagents or enzyme preparations in the practice of this invention, concentrations of pyridoxal phosphate or other cofactor in those solutions and preparations are preferably in the range of from about 0.005 mM to about 1 mM. As mentioned, derivatives of pyridoxal phosphate may also be used in the practice of this invention. An example of a derivative of pyridoxal phosphate is described in J. D. Rozzell, Methods in Enzymology, 136: 479–497 (1987), the disclosure of which is incorporated herein by reference.

In the practice of this invention, the total amount of 2-ketobutyrate produced by the action of methionine gamma-lyase on L-homocysteine and/or L-methionine may be determined by any method known in the art, preferably by using a 2-ketobutyrate detecting agent. As used herein, the term "2-ketobutyrate detecting agent" refers to an agent that is capable of chemically reacting with 2-ketobutyrate in a manner permitting the quantitation of 2-ketobutyrate. Nonlimiting examples of 2-ketobutyrate detecting agents include 2,4-dinitrophenylhydrazine and lactic dehydrogenase combined with its cofactor NADH. In one embodiment of the present invention, 2-ketobutyrate is detected by reaction with 2,4-dinitrophenylhydrazine, producing a highly colored 2,4-phenylhydrazone, which can be measured at a wavelength between 400 nm and 550 nm. Other hydrazines that also produce hydrazone derivatives with 2-ketobutyrate may be used if desired.

In an especially preferred embodiment, 2-ketobutyrate is detected by monitoring spectrophotometrically the oxidation of reduced nicotinamide cofactor, NADH, catalyzed by the enzyme lactic dehydrogenase. An example of the use of this method for the determination of pyruvate is described in the 1998 Sigma catalog, p. 2629, the disclosure of which is incorporated herein by reference. This method may be similarly used to determine the total amount of 2-ketobutyrate present because 2-ketobutyrate is also a substrate for lactic dehydrogenase. The 2-ketobutyrate produced by the action of methionine gamma-lyase on L-homocysteine and/or L-methionine is contacted with a reagent containing NADH, or a derivative thereof, and lactic dehydrogenase. The total amount of oxidation of NADH to NAD+ is then determined. As used herein, the term "derivatives," with respect to cofactors, refers to salts, solvates, and other chemically modified forms that retain cofactor activity.

A convenient way to measure the oxidation of NADH, or derivative thereof, is by measuring the change in absorbance at 340 nm. Another method for measuring NADH oxidation is by measurement of fluorescence, as described by Passoneau and Lowry in Enzymatic Analysis, A Practical Guide, pp. 219–222, 1993, the disclosure of which is incorporated herein by reference. In one embodiment, NADH and lactic dehydrogenase are included in the reagent comprising methionine gamma-lyase and pyridoxal phosphate. The concentration of NADH in the reagent preferably ranges from about 0.01 mM to about 5 mM, and more preferably from about 0.05 mM to about 1 mM. In this embodiment, lactic dehydrogenase from any of a number of sources may be used, and the lactic dehydrogenase may be either D-lactic dehydrogenase or L-lactic dehydrogenase. Some sources of lactic dehydrogenase may be found in the Sigma Catalog, 1998, pp. 659–661, the disclosure of which is incorporated herein by reference. These sources include rabbit muscle, horse muscle, porcine muscle, bovine heart, porcine heart, bacteria of the genus Lactobacillus, and the like. Alternatively, the reagent containing NADH, or a derivative thereof, and lactic dehydrogenase may be prepared separately from the mixture containing methionine gamma-lyase. In such a case, an amount of the reaction mixture containing 2-ketobutyrate produced from L-homocysteine and/or L-methionine by the action of methionine gamma-lyase is added to the NADH/lactic dehydrogenase reagent, and the total amount of oxidation of NADH is measured.

In another embodiment of this invention, NADH, or a derivative thereof, reacts with 2-ketobutyrate in the presence of lactic dehydrogenase to form NAD+, which further reacts with a dye capable of producing a color change, preferably in the visible range, when oxidized. If the amount of NADH used in the assay is less than the amount of L-homocysteine and/or L-methionine in the test solution, the NAD+ may be recycled to NADH by reduction using an excess amount of the dye. The recycled NADH would then be available to react with additional molecules of 2-ketobutyrate as necessary. In this case, the color change of the dye may be used to determine the total amount of oxidation of NADH to NAD+, i.e., that amount corresponding to the total amount of 2-ketobutyrate reduced by the original amount of NADH plus any NADH produced by recycling of NAD+. Nonlimiting examples of dyes useful in the invention include 2,6-dichlorophenolindophenol, tetrazolium compounds, phenazine methosulfate, methyl viologen and derivatives thereof. In an especially preferred embodiment, a sample containing L-homocysteine and/or L-methionine is added to a solution containing methionine gamma-lyase, pyridoxal phosphate, NADH, lactic dehydrogenase, diaphorase, and reduced 2,6-dichlorophenolindophenol, which is colorless. The 2-ketobutyrate formed by the action of methionine gamma-lyase on L-homocysteine and/or L-methionine is reduced by lactic dehydrogenase, with concomitant oxidation of NADH to NAD+; the NAD+ oxidizes the reduced form of 2,6-dichlorophenolindophenol in the presence of the enzyme diaphorase, producing a blue color, the intensity of which is measured spectrophotometrically. This embodiment is also particularly useful in the construction of a rapid calorimetric test for the detection of the presence of L-homocysteine and/or L-methionine in a solution such as urine or blood. The intensity of the color observed in the test solution is compared to the colors produced in a set of standard solutions of L-homocysteine and/or L-methionine. The amount of L-homocysteine and/or L-methionine present in the test solution can then be estimated based on the relative intensity of the observed color compared to the standards.

Because 2-ketobutyrate is produced in equimolar amounts, relative to the amount of L-homocysteine and/or L-methionine acted on by methionine gamma-lyase, measurement of the amount of L-homocysteine and/or L-methionine present in a solution may be conveniently accomplished by measuring the amount of 2-ketobutyrate produced by the action of methionine gamma-lyase on L-homocysteine and/or L-methionine. Preferably, the reaction is permitted to proceed to substantial completion in order to quantitate the total amount of 2-ketobutyrate produced. One skilled in the art can determine when the reaction is substantially complete, for example, when no further oxidation of NADH to NAD+ occurs or when no further color change occurs, in the case of reaction with a dye. If desired, however, the concentration of L-homocysteine and/or L-methionine can be determined when the reaction does not proceed to substantial completion. Specifically, a set of comparison samples can be prepared where the amount of 2-ketobutyrate formed is determined after a known period of time. A curve can be plotted providing 2-ketobutyrate concentration versus L-homocysteine and/or L-methionine concentration. The amount of 2-ketobutyrate formed in the test sample is then compared to the comparison samples that were reacted for the same amount of time, and the amount of L-homocysteine and/or L-methionine is determined by interpolation.

It is possible that samples to be assayed for L-homocysteine and/or L-methionine could contain pyruvate, 2-ketobutyrate, or other 2-ketoacids that would interfere with the accurate determination of the amount of 2-ketobutyrate formed by the action of methionine gamma-lyase. Should this be the case, the pyruvate, 2-ketobutyrate, and/or other 2-ketoacids may be first eliminated by treating the solution, before contacting it with the reagent containing methionine gamma-lyase, with an agent capable of converting pyruvate, 2-ketobutyrate and any other 2-ketoacids present in the solution to compounds that will not react with the 2-ketobutyrate detecting agent. Suitable agents include, for example, borohydride reducing agents, lactic dehydrogenase in the presence of NADH, and 2,4-dinitrophenylhydrazine. In this way, only the 2-ketobutyrate formed by reaction of L-homocysteine and/or L-methionine with methionine gamma-lyase will be measured.

In a preferred embodiment of the invention, methionine gamma-lyase, or a derivative thereof, is immobilized, such as on a support material, to produce a support-bound form of the enzyme that may be used to detect the presence or absence of L-homocysteine and/or L-methionine in a solution with which the immobilized enzyme is contacted. Methionine gamma-lyase, or a derivative thereof, may be either covalently or noncovalently immobilized. Examples of methods for the immobilization of enzymes in general, and methionine ganma-lyase in particular, that may be used in the practice of this invention are described by Rozzell in "Biocatalytic Production of Amino Acids and Derivatives," D. Rozzell and F. Wagner, editors, Hanser Publishers, Munich (1992), pp. 279–319, the disclosure of which is incorporated herein by reference. Nonlimiting examples of support materials include paper, filter paper, nylon, glass, ceramic, silica, alumina, diatomaceous earth, cellulose, Eupergit™, polymethacrylate, polypropylene, polystyrene, polyethylene, polyvinylchloride, and derivatives thereof. Preferably a 2-ketobutyrate detecting agent is also immobilized on the support material.

When immobilized methionine gamma-lyase is used in the practice of this invention, the same types of detection methods described earlier may be employed to measure the amount of L-homocysteine and/or L-methionine converted to 2-ketobutyrate. In a preferred embodiment, the methionine gamma-lyase, or derivative thereof, and lactic dehydrogenase are immobilized on a support material that also contains or has adsorbed or absorbed the pyridoxal phosphate and NADH cofactors, and the support bound enzymes are contacted with a solution containing L-homocysteine and/or L-methionine. For visualization, a dye such as 2,4-dichlorophenolindophenol, a tetrazolium, phenazine methosulfate, or methyl viologen may also be impregnated in or otherwise added to the support-bound enzymes. The dyes change color upon reaction with NAD+, which is produced by reduction of 2-ketobutyrate by NADH catalyzed by lactic dehydrogenase. To accelerate color development, the enzyme diaphorase may be coimmobilized with the other enzymes or added to the support bound enzymes, if desired. This embodiment of the invention is especially useful in a test strip or dipstick assay that could be carried out conveniently at home or in a doctor's office for monitoring of L-homocysteine and/or L-methionine.

In another embodiment of this invention, the color reaction described above for an immobilized enzyme test may also be used in solution to measure L-homocysteine and/or L-methionine. The color change by the dye may be observed visually, for qualitative determination of L-homocysteine and/or L-methionine, or alternatively, the color may be measured spectrophotometrically for quantitative measurement of L-homocysteine and/or L-methionine. As with the immobilized enzymes, diaphorase may be added to the solution, if desired, to accelerate the development of the color.

In carrying out the methods of the present invention, the temperature preferably ranges from about 4° C. to about 95° C., and more preferably from about 15° C. to about 45° C. The pH of the assay mixture is preferably maintained in the range of from about 3 to about 12, and more preferably in the range of from about 4.5 to about 10.5. To maintain proper pH during the practice of the present invention, buffers may be used, if desired. Nonlimiting examples of buffers that may be used in the practice of this invention include inorganic buffers such as phosphate, borate, carbonate, and the like, provided as their lithium, sodium, potassium, or ammonium salts. Other buffers that may be used include organic buffers such as tris-(hydroxymethyl) aminomethane (commonly referred to as Tris), 3-(N-morpholino) ethanesulfonic acid (commonly referred to as MES), 3-(N-morpholino) propanesulfonic acid (commonly referred to as MOPS), and the like.

The methods of the present invention can also be used for solutions containing homocystine or a mixed disulfide containing half homocystine. Prior to contacting the solution with the reagent comprising methionine gamma-lyase, the solution is treated with a reducing agent to reduce substantially all L-homocystine and mixed disulfides containing half homocystine present in the solution to produce L-homocysteine. The addition of a reducing agent to such mixtures liberates homocysteine by reduction of the disulfide bond in homocystine or in a mixed disulfide containing half-homocystine as one of its components. As used herein, the phrase "substantially all" refers to at least 60%, preferably at least 80%, and more preferably at least 90%. Particularly preferred reducing agents are borohydride salts and thiol reducing agents, such as β-mercaptoethanol, dithiothreitol, dithioerythritol, and thioacetic acid and salts thereof. Such reducing agents, when added, are preferably present in the assay mixture at a concentration of from about 0.5 mg/ml to about 25 mg/ml.

In cases where L-homocysteine is substantially in its disulfide or mixed disulfide form, and virtually no L-homocysteine is present, one can determine the individual amounts of L-methionine and L-homocystine (and mixed disulfide containing half homocystine). For example, in certain samples of biological origin such as urine, L-homocysteine may often be present already partially or completely oxidized to its disulfide (L-homocystine) or to a mixed disulfide formed with other thiol-containing compounds. A convenient method for making this determination is to divide the sample to be assayed into two portions. The first portion is assayed as previously described to determine the amount of L-methionine present. The second portion is first treated with a reducing agent, such as a thiol reducing agent as discussed above, so that substantially all disulfide bonds are reduced, and the assay is carried out to determine the total amount of L-methionine plus L-homocysteine. The amount of L-homocysteine present is defined by the difference in the values obtained in the two separate assays. The amount of L-homocystine present in the original solution can also be determine because each mole of L-homocystine produces 2 moles of L-homocysteine after reduction. Similarly, the amount of mixed disulfides containing half homocystine can be determined because each mole of mixed disulfide produces 1 mole of L-homocysteine after reduction. Of course, one can measure the total amount of L-methionine and L-homocysteine combined using this general method by using a single sample and reducing the disulfide bonds prior to contacting the sample with L-methionine gamma-lyase.

Even when the solution to be assayed contains L-methionine and L-homocysteine, the individual amounts of each of these components can be determined by taking advantage of the fact that methionine gamma-lyase acts on L-homocysteine, but not its oxidized form L-homocystine. As an example, a solution containing unknown amounts of both amino acids is treated to insure that all L-homocysteine is in its oxidized, disulfide form L-homocystine, or as a mixed disulfide with another thiol-containing compound, for example, by exposure to air or oxygen for a sufficient time. Such oxidation may also be accomplished by other means known in the art. Once a solution containing L-methionine and L-homocystine or a mixed disulfide has been obtained, the methods of the present invention may be used to determine the amount of L-methionine in the solution or mixture. After the amount of L-methionine has been determined, the solution is treated with a thiol reducing agent, or other reducing agent, so that substantially all the L-homocysteine present is liberated from disulfides and mixed disulfides, and the method is repeated to determine the amount of L-homocysteine. In this way, the amount of both L-methionine and L-homocysteine may be individually determined.

In accord with this invention, the methionine gamma-lyase may be used as a crude enzyme preparation, a partially purified enzyme preparation, or as a pure homogeneous enzyme. The enzyme may be obtained from any source that provides a methionine gamma-lyase with activity on L-homocysteine and/or L-methionine, but little or no activity on L-cysteine, L-cystine, and other amino acids. Preferably, the methionine gamma-lyase also has a Km for L-methionine and L-homocysteine of about 1 mM or less. Useful sources of the enzyme include psychrophilic, mesophilic, and thermophilic organisms, and various species of plants and animals containing the methionine metabolic pathway that produces 2-ketobutyrate and methanethiol from L-methionine. Nonlimiting sources of methionine gamma-lyase useful in the practice of this invention include *Pseudomonas putida*, Aeromonas sp., *Brevibacterium casei*, *Pseudomonas ovalis*, *Bacillus subtilis*, *Bacillus stearothermophilus*, *Klebsiella aerogenes*, *Proteus rettgeri*, Alcaligenes sp., and the like. In an especially preferred embodiment, the source of methionine gamma-lyase is *Pseudomonas putida* ICR 3460, described by Nakayama et al, Anal. Biochem., 138: 421 (1984), the disclosure of which is incorporated herein by reference, *Pseudomonas ovalis*, *Pseudomonas putida* ATCC 8209, available from the American Type Culture Collection, or *Brevibaeterium casei* ATCC 35513, also available from American Type Culture Collection. The genes encoding any useful methionine gamma-lyases, or derivatives thereof, may also be cloned using techniques well-known in the art, if desired.

As a stabilizer, an alkali metal salt of azide (for example, sodium azide or potassium azide) may be added to any of the reagents. Preferably, the alkali metal salt of azide is present in a concentration of from about 0.5 to about 20 millimoles per liter of total reagent.

The invention will now be further described by the following examples, which are presented here for illustrative purposes only and are not intended to limit the scope of the invention.

EXAMPLES

Example 1

Growth of Cells Containing Methionine Gamma-lyase Activity

*Pseudomonas putida* ICR 3460 is cultivated in 2 liter shake flasks according to the procedure of Nakayama et al. Anal. Biochem., 138: 421 (1984), the disclosure of which is incorporated herein by reference. Growth is monitored by following the $OD_{600}$ of the culture. Once stationary phase is achieved, the cells are harvested by centrifugation at 13,000 g using a Beckman centrifuge and washed with 50 mM potassium phosphate buffer, pH 7.0, containing 0.1 mM dithiothreitol and 0.01 mM pyridoxal phosphate. Cells not processed immediately may be stored at −70° C. until needed.

Example 2

Alternative Growth of Cells Containing Methionine Gamma-lyase Activity

Aeromonas sp. is cultivated in 2 liter shake flasks according to the procedure of Nakayama, Agric. Biol. Chem., 48: 1991 (1984), the disclosure of which is incorporated herein by reference. Growth is monitored by following the $OD_{600}$ of the culture. Once stationary phase is achieved, the cells are harvested by centrifugation at 13,000 g using a Beckman centrifuge and washed with 50 mM potassium phosphate buffer, pH 7.0, containing 0.1 mM dithiothreitol and 0.01 mM pyridoxal phosphate. Cells not processed immediately may be stored at −70° C. until needed.

Example 3

Alternative Growth of Cells Containing Methionine Gamma-lyase Activity

*Brevibacterium casei* ATCC 35513 is cultivated in 2 liter shake flasks according to the procedure described in J. Gen Microbiol. 101: 345–349 (1977), the disclosure of which is incorporated herein by reference. Growth is monitored by following the $OD_{600}$ of the culture. Once stationary phase is achieved, the cells are harvested by centrifugation at 13,000 g using a Beckman centrifuge and washed with 50 mM potassium phosphate buffer, pH 7.0, containing 0.1 mM dithiothreitol and 0.01 mM pyridoxal phosphate. Cells not processed immediately may be stored at −70° C. until needed.

Example 4

Quantitation of the Amount of 2-ketobutyrate Using Lactic Dehydrogenase and NADH The spectrophotometric determination of 2-ketobutyrate concentrations in a solution is accomplished by the reduction of 2-ketobutyrate with NADH catalyzed by the enzyme lactic dehydrogenase.

Stock solutions for the spectrophotometric quantitation of 2-ketobutyrate are prepared as follows:

Potassium phosphate buffer, 100 mM, pH 8.0

NADH in deionized water, 5 mg/ml

Lactate dehydrogenase, crystalline suspension from rabbit muscle in 3.2M ammonium sulfate containing 9.6 mg protein/ml, with a specific activity of 800–1200 units per milligram (Sigma)

2-Ketobutyrate sodium salt (Sigma) in deionized water, 10 mM.

To 0.97 ml of potassium phosphate buffer is added 30 microliters of NADH solution and 5 microliters of lactate dehydrogenase suspension. After mixing by inversion, a background reading of the absorbance at 340 nm is taken, and any background rate of NADH oxidation is noted. An aliquot of 2-ketobutyrate solution is added, and the change in absorbance at 340 nm is measured and compared to the known amount of 2-ketobutyrate added. The volume of the aliquots withdrawn is varied from 10 microliters to 150 microliters so that the final concentration of 2-ketobutyrate in the solution is in the range of from approximately 0.01 mM to about 0.15 mM. Using the molar extinction coefficient of $6,200 M^{-1} cm^{-1}$ and cuvettes with a 1 ml volume and a 1 cm path length, the total amount of 2-ketobutyrate in the cuvette is calculated from Beer's Law using the equation:

Concentration of 2-ketobutyrate in mM =

$$\frac{\text{Change in Absorbance at 340 nm}}{6.2}$$

The accuracy of the assay is determined by comparing the amount of 2-ketobutyrate measured by spectrophotometric assay to the known amount added to the test sample. Representative results are shown in Table 1.

TABLE 1

| 2-Ketobutyrate Concentration Added | 2-Ketobutyrate Concentration by Assay |
| --- | --- |
| 0.01 mM | 0.01 mM |
| 0.02 mM | 0.02 mM |
| 0.04 mM | 0.04 mM |
| 0.08 mM | 0.077 mM |
| 0.12 mM | 0.115 mM |
| 0.15 mM | 0.155 mM |

Example 5
Isolation and Purification of Methionine Gamma-lyase

*Pseudomonas putida* ICR 3460 cell paste containing methionine gamma-lyase is mixed with two volumes of cold 50 mM potassium phosphate buffer, pH 7.0, containing 0.1 mM dithiothreitol and 0.01 mM pyridoxal phosphate (purification buffer), and lysed, for example, by passing through a Microfluidizer (Microfluidics Corporation, Newton, Mass). Cell debris is removed by centrifugation at 13,000 g for 30 minutes. The clarified enzyme solution is loaded onto a DEAE-sepharose fast flow column equilibrated with the purification buffer, and the column is washed with purification buffer until no more protein is detected in the eluent from the column. The column is then eluted with a linear gradient of 0–0.5M NaCl in purification buffer, pooling fractions containing methionine gamma-lyase activity. The active fractions are dialyzed against purification buffer containing 1M $(NH_4)_2SO_4$ and then loaded onto a Phenyl Sepharose column, followed by elution with a 1.0 to 0M linear gradient of $(NH_4)_2SO_4$. Active fractions are again pooled and dialyzed against purification buffer. The enzyme solution can be stored at 4° C. in the presence of 0.02% sodium azide for several weeks. For longer term storage, the enzyme solution can be mixed with an equal volume of glycerol and stored at −20 ° C.

The methionine gamma-lyase activity is assayed by monitoring the rate of breakdown of L-methionine into 2-ketobutyrate. The 2-ketobutyrate produced in the reaction is quantitated by reaction with lactic dehydrogenase and NADH, and the rate of decrease in the absorbance at 340 nm is monitored.

Stock solutions for the coupled spectrophotometric assay are prepared as follows:

Potassiumphosphate buffer, 100 mM, pH 8.0 containing 0.01 mM pyridoxal 5'-phosphate NADH in deionized water, 5 mg/ml Lactate dehydrogenase, crystalline suspension from rabbit muscle in 3.2M ammonium sulfate containing 9.6 mg protein/ml, with a specific activity of 800–1200 units per milligram (Sigma)

L-methionine in 0.02M HCl, 10 mM

The assay mixture is prepared as follows:

To a cuvette containing 0.76 ml of 50 mM potassium phosphate buffer, pH 8.0, 0.01 mM pyridoxal phosphate, 0.005 ml lactic dehydrogenase suspension, and 0.030 ml NADH solution was added 0.2 ml of 10 mM L-methionine solution in 0.01M HCl. A background reading of the absorbance at 340 nm was made. Enzyme solution (10 microliters, appropriately diluted to produce a change of absorbance at 340 nm between 0.1 and 1 absorbance unit per minute) is then added, and the rate of decrease in the absorbance at 340 nm is measured using a spectrophotometer. Based on the molar extinction coefficient of 6,200$M^{-1}$ $cm^{-1}$ for NADH, the rate of formation of 2-ketobutyrate from L-methionine is calculated.

One unit of methionine gamma-lyase activity is that amount of enzyme that causes the oxidation of 1 micromole of NADH per minute at room temperature under the assay conditions described above. Purified methionine gamma-lyase has a specific activity of approximately 20 units per milligram when assayed as above using L-methionine as substrate.

This procedure may be repeated for isolation and purification of methionine gamma-lyase from *Brevibacterium casei* ATCC 35513, *Pseudomonas putida* ATCC 8209, and *Pseudomonas ovalis* IFO 3738.

Example 6
Demonstration of the Reactivity of L-homocysteine as a Substrate for the Enzyme Methionine Gamma-lyase.

The assay of the activity of L-homocysteine as a substrate for methionine gamma-lyase is carried out as described above for L-methionine, but replacing L-methionine with L-homocysteine. With L-homocysteine as a substrate at a concentration of 2.5 mM and using methionine gamma-lyase from *Pseudomonas putida* ICR 3460, the activity of the purified methionine gamma-lyase is approximately 36 units per milligram.

Example 7
Determination of the Catalytic Efficiency of Methionine Gamma-lyase on L-homocysteine Relative to L-methionine.

Kinetic measurements using methionine gamma-lyase purified from *Pseudomonas putida* ICR 3460, as reported by Nakayama et al., are as follows:

|  | L-Methionine | L-Homocysteine |
| --- | --- | --- |
| Km | 1.0 mM | 0.43 mM |
| Vmax | 20.4 micromole/min-mg | 36 micromole/min-mg |

The molecular weight of the subunit of the enzyme based on the molecular weight determination reported by Nakayama et al. is approximately 43,000. Using these data, the term for catalytic efficiency Vmax/Km is calculated as follows for both L-methionine and L-homocysteine:

For L-methionine:

Vmax=20.4 micromole $min^{-1}mg^{-1}$*43 mg $micromole^{-1}$*1 min/60 sec=15 $sec^{-1}$ Vmax/Km=15 $sec^{-1}$/1.0 mM=15 $mM^{-1}sec^{-1}$ For L-homocysteine:

Vmax=36 micromole $min^{-1}$*43 mg $micromole^{-1}$*1 min/60 sec=26 $sec^{-1}$ Vmax/Km=26 $sec^{-1}$/0.43 mM=60 $mM^{-1}sec^{-1}$ These calculations show that both L-methionine and L-homocysteine are good substrates for the enzyme from *Pseudomonas putida*. Furthermore, the Km for both L-methionine and L-homocysteine is 1 mM or less, indicating that both compounds are acted on efficiently at low concentrations, enabling the reaction to proceed rapidly to substantial completion.

Example 8
Demonstration of a Coupled Enzyme Assay to Quantitate L-homocysteine and L-methionine in Solution Using Methionine Gamma-lyase and Lactate Dehydrogenase The spectrophotometric measurement of L-homocysteine and/or L-methionine concentrations in urine is accomplished by coupling of the reaction catalyzed by the enzyme methionine gamma-lyase, which produces 2-ketobutyrate, to the reduction of 2-ketobutyrate catalyzed by the enzyme lactate dehydrogenase described in Example 4.

Stock solutions for the coupled spectrophotometric assay are prepared as follows:

Potassium phosphate buffer, 100 mM, pH 8.0, containing 0.01 mM pyridoxal 5'-phosphate NADH in deionized water, 5 mg/ml Methionine gamma-lyase solution, 200 units per milliliter Lactate dehydrogenase, crystalline suspension from rabbit muscle in 3.2M ammonium sulfate containing 9.6 mg protein/ml, with a specific activity of 800–1200 units per milligram (Sigma)

L-Methionine in 0.02M HCl, 10 mM

L-Homocysteine in 0.02M HCl, 10 mM

L-Methionine (5 mM) and L-homocysteine (5 mM) solution in 0.02M HCl

To 0.95 ml of potassium phosphate buffer containing 0.01 mM pyridoxal phosphate is added 30 microliters of NADH solution, 20 microliters of methionine gamma-lyase solution, and 5 microliters of lactate dehydrogenase suspension. After mixing by inversion, a background reading of the absorbance at 340 nm is taken, and any background rate of NADH oxidation is noted. An aliquot of the amino acid substrate solution (L-methionine, L-homocysteine, mixture of L-methionine and L-homocysteine) is added in appropriate dilutions, and the change in absorbance at 340 nm is measured and compared to the known concentration of amino acid substrate added. For determination of higher concentrations of L-methionine or L-homocysteine, mixtures of the amino acid substrate in buffered solution (the reaction mixture) containing 0.01 mM pyridoxal phosphate are prepared. After the addition of methionine gamma-lyase, aliquots of the reaction mixture are withdrawn at time intervals, and diluted into the assay solution described above. The volume of the aliquot withdrawn is chosen so that the concentration of 2-ketobutyrate produced at 100% conversion of the amino acid substrate in the reaction mixture is in the range of from about 0.01 mM to about 2.0 mM. The change in absorbance at 340 nm is measured. For example, using the molar extinction coefficient of $6,200 M^{-1} cm^{-1}$ and cuvettes with a 1 ml volume and a 1 cm path length, the total amount of L-methionine and/or L-homocysteine converted into 2-ketobutyrate is calculated from Beer's Law using the equation $$\text{Concentration} = \frac{\text{Change in Absorbance at 340 nm * Dilution factor}}{6.2}$$

where the dilution factor is equal to 1 divided by the aliquot volume in ml.

The amount of L-methionine and/or L-homocysteine determined by assay is compared to the known amounts of amino acid substrate added. Representative results that may be obtained from assays carried out as above are shown in the Tables 2–4 below.

TABLE 2

| L-Homocysteine Concentration in Standard | L-homocysteine Concentration Determined by Assay |
| --- | --- |
| 0.05 mM | 0.05 mM |
| 0.10 mM | 0.10 mM |
| 0.50 mM | 0.48 mM |
| 1.00 mM | 0.99 mM |
| 5.00 mM | 5.1 mM |
| 10.0 mM | 9.9 mM |

TABLE 3

| L-Methionine Concentration in Standard | L-Methionine Concentration Determined by Assay |
| --- | --- |
| 0.05 mM | 0.05 mM |
| 0.10 mM | 0.10 mM |
| 0.50 mM | 0.49 mM |
| 1.00 mM | 0.95 mM |
| 5.00 mM | 5.0 mM |
| 10.0 mM | 10.1 mM |

TABLE 4

| L-Homocysteine + L-Methionine Concentration in Standard | L-Homocysteine + L-Methionine Concentration Determined by Assay |
| --- | --- |
| 0.05 mM | 0.05 mM |
| 0.10 mM | 0.10 mM |
| 0.50 mM | 0.50 mM |
| 1.00 mM | 1.05 mM |
| 5.00 mM | 5.2 mM |
| 10.0 mM | 10.3 mM |

Example 9

Demonstration of a Coupled Enzyme Assay to Quantitate L-homocysteine and L-methionine in Urine Using Methionine Gamma-lyase and Lactate Dehydrogenase Urine samples into which L-methionine, L-homocysteine, and both L-methionine and L-homocysteine are added at concentrations of 10 mg/L, 25 mg/L, 75 mg/L, 150 mg/L, 300 mg/L, and 600 mg/L are prepared, the samples are treated with a borohydride reducing agent to reduce all 2-ketoacids present, and the concentrations of the added L-homocysteine and/or L-methionine are determined by assay as described in Example 8. Representative results are shown in the Tables 5 to 7 below.

TABLE 5

| L-Methionine Concentration Added to Urine | L-Methionine Concentration Determined by Assay |
| --- | --- |
| 10 mg/L | 10 mg/L |
| 25 mg/L | 27 mg/L |
| 75 mg/L | 75 mg/L |
| 150 mg/L | 150 mg/L |
| 300 mg/L | 305 mg/L |
| 600 mg/L | 595 mg/L |

TABLE 6

| L-Homocysteine Concentration Added to Urine | L-Homocysteine Concentration Determined by Assay |
| --- | --- |
| 10 mg/L | 10 mg/L |
| 25 mg/L | 26 mg/L |
| 75 mg/L | 78 mg/L |
| 150 mg/L | 155 mg/L |
| 300 mg/L | 310 mg/L |
| 600 mg/L | 600 mg/L |

TABLE 7

| L-Homocysteine + L-Methionine Concentration Added to Urine | L-Homocysteine + L-Methionine Concentration Determined by Assay |
| --- | --- |
| 10 mg/L | 10 mg/L |
| 25 mg/L | 25 mg/L |
| 75 mg/L | 80 mg/L |
| 150 mg/L | 155 mg/L |
| 300 mg/L | 315 mg/L |
| 600 mg/L | 620 mg/L |

Example 10
Demonstration of a Coupled Enzyme Assay to Quantitate L-homocysteine and L-methionine in Blood Using Methionine Gamma-lyase and Lactate Dehydrogenase Blood specimens are diluted into 3 volumes of 50 mM potassium phosphate buffer, pH 7.0, and L-methionine, L-homocysteine, and both L-methionine and L-homocysteine are added to achieve final concentrations of 10 mg/L, 25 mg/L, 75 mg/L, 150 mg/L, 300 mg/L, and 600 mg/L. The concentrations are determined by assay as described in Example 8. Representative results are shown in the Tables 8 to 10 below.

TABLE 8

| L-Methionine Concentration Added to Blood Sample | L-Methionine Concentration Determined by Assay |
| --- | --- |
| 10 mg/L | 10 mg/L |
| 25 mg/L | 25 mg/L |
| 75 mg/L | 77 mg/L |
| 150 mg/L | 160 mg/L |
| 300 mg/L | 305 mg/L |
| 600 mg/L | 610 mg/L |

TABLE 9

| L-Homocysteine Concentration Added to Blood Sample | L-Homocysteine Concentration Determined by Assay |
| --- | --- |
| 10 mg/L | 10 mg/L |
| 25 mg/L | 25 mg/L |
| 75 mg/L | 80 mg/L |
| 150 mg/L | 160 mg/L |
| 300 mg/L | 310 mg/L |
| 600 mg/L | 630 mg/L |

TABLE 10

| L-Homocysteine + L-Methionine Concentration Added to Blood Sample | L-Homocysteine + L-Methionine Concentration Determined by Assay |
| --- | --- |
| 10 mg/L | 10 mg/L |
| 25 mg/L | 26 mg/L |
| 75 mg/L | 79 mg/L |
| 150 mg/L | 155 mg/L |
| 300 mg/L | 315 mg/L |
| 600 mg/L | 625 mg/L |

Example 11
Cloning of the Gene for Methionine Gamma-lyase from Pseudomonas sp.

The gene for methionine gamma-lyase from *Pseudomonas ovalis, Pseudomonas putida*, or *Brevibacterium casei* may be cloned by techniques and methods well-known in the art. Such techniques are explained fully in the literature. See, for example, J. Sambrook et al., "Molecular Cloning; A Laboratory Manual" (1989); "DNA Cloning", Vol. I and II (D. N. Glover ed. 1985); "Oligonucleotide Synthesis" (M. J. Gait ed, 1984); "Nucleic Acid Hybridization" (B. D. Hames & S. J. Higgins eds. 1984); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984); the series, "Methods In Enzymology" (Academic Press, Inc.); "Gene Transfer Vectors For Mammalian Cells" (J. H. Miller and M. P. Calos eds., 1987, Cold Spring Harbor Laboratory); and "Methods in Enzymology" volumes 154 and 155 (Wu and Grossman, and Wu, eds., respectively 1987); the disclosures of which are incorporated herein by reference.

Example 12
Immobilization of Methionine Gamma-lyase

Methionine gamma-lyase may be immobilized by the following procedure. Three hundred grams of silica particles (Zeosil, Rhone Poulenc; 1.0–1.5 mm diameter) are placed in a large beaker and suspended in 800 ml of deionized water. Five hundred milliliters of an aqueous solution of 5% polyethyleneimine (w/v) is added, and the suspension is mixed periodically by swirling or by stirring gently with a large spatula. After 4 hours, the suspension is suction filtered, washed with 2 liters of deionized water, and left overnight in a shallow pan to dry. The air-dried polyethyleneimine-treated silica is activated with 900 ml of an aqueous solution of 2.5% glutaraldehyde in 50 mM potassium phosphate buffer, pH 7.0 with gentle, occasional agitation for 1 hour. The silica takes on a brownish color during the glutaraldehyde treatment. The activated silica matrix is recovered by suction filtration, washed with 5×1 liter of 50 mM potassium phosphate buffer, pH 7.0, and may be stored moist at 4° C. until ready for use.

Immobilization of methionine gamma-lyase is accomplished by adding 300 ml of a clarified solution of the enzyme in 50 mM potassium phosphate buffer, pH 7.0, containing 0.1 mM pyridoxal phosphate (50 mg protein/ml as determined by the Bradford protein assay, Sigma Chemical Company) to 100 grams of the activated silica matrix, and gently agitating the resulting suspension for 1 hour. The unbound protein solution is decanted off, and the immobilized enzyme is washed with 50 mM potassium phosphate buffer, pH 7.0 containing 0.3M NaCl(4×1 liter). The immobilized methionine gamma-lyase may be stored as a suspension in 50 mM potassium phosphate buffer, pH 7.0, containing 0.02% sodium azide as stabilizer at 4° C.

Example 13
Alternative Immobilization of Methionine Gamma-lyase

Methionine gamma-lyase may be immobilized to an epoxy-activated methacrylate polymer by the following procedure. Ten grams of Eupergit (Rohm Pharma, Darmstadt, Germany) is suspended in 100 ml of 50 mM potassium phosphate buffer, pH 7.0, and a solution of methionine gamma-lyase (50 mg in 20 ml of 50 potassium phosphate buffer, pH 7.0, containing 0.1 mM pyridoxal phosphate) is added. The suspension is mixed gently for 24 hours on an orbital shaker, and the solution of unbound protein is decanted off. The resulting immobilized enzyme is washed with 50 mM potassium phosphate buffer, pH 7.0, containing 0.3M NaCl (4×100 ml). The immobilized methionine gamma-lyase may be stored as a suspension in 50 potassium phosphate buffer, pH 7.0, containing 1 mM dithiothreitol and 0.02% sodium azide as stabilizer at 4° C.

Example 14
Immobilization of Methionine Gamma-lyase on Filter Paper

Methionine gamma-lyase may be immobilized on filter paper filter paper by the following method. Filter paper (Whatman) is soaked in a solution of methionine gamma-lyase (50 mg in 20 ml of 50 mM potassium phosphate buffer, pH 7.0, containing 0.1 mM pyridoxal phosphate and 0.02% sodium azide as stabilizer), and the filter paper is placed on a paper towel and allowed to drain for approximately 10 minutes. The damp filter paper containing methionine gamma-lyase is stored at 4° C. until needed.

Example 15
Alternative Immobilization of Methionine Gamma-lyase on Filter Paper Filter paper (Whatman) is soaked in an aqueous solution of 5% polyethyleneimine (w/v) for 30 minutes. The filter paper is removed, drained on a paper towel, washed with an aqueous buffer of 50 mM potassium phosphate buffer, pH 7.0, and placed in an aqueous solution of 2.5% glutaraldehyde in 50 mM potassium phosphate buffer, pH 7.0 for 1 hour. The filter paper is then removed from the glutaraldehyde solution, washed with 50 mM potassium phosphate buffer, pH 7.0, and then immersed in a solution of methionine gamma-lyase (50 mg in 20 ml of 50 mM potassium phosphate buffer, pH 7.0, containing 0.1 mM pyridoxal phosphate and 0.02% sodium azide as stabilizer). The enzyme solution containing the activated filter paper is gently agitated by occasional rocking for 1 hour. At the end of this time, the filter paper containing immobilized methionine gamma-lyase is placed on a paper towel, allowed to drain, and then stored at 4° C. until needed.

The preceding description has been presented with reference to presently preferred embodiments of the invention. Workers skilled in the art and technology to which this invention pertains will appreciate that alterations and changes in the described methods and compositions may be practiced without meaningfully departing from the spirit and scope of this invention.

Accordingly, the foregoing description should not be read as pertaining only to the precise methods and compositions described, but rather should be read consistent with and as support to the following claims, which are to have their fullest and fair scope.

What is claimed is:

1. A method for measuring the amount of L-homocysteine and/or L-methionine in a solution comprising:
   (a) contacting the solution containing L-homocysteine and/or L-methionine with a reagent comprising methionine gamma-lyase, or a derivative thereof, and a cofactor capable of forming a Schiff base with the L-methionine and/or L-homocysteine, for a time sufficient to catalyze the reaction of L-homocysteine and/or L-methionine to form 2-ketobutyrate;
   (b) determining the amount of 2-ketobutyrate formed by oxidizing NADH, or a derivative thereof, to NAD+, or a derivative thereof, in the presence of the enzyme lactic dehydrogenase, or a derivative thereof, and determining the total amount of oxidation of NADH, or a derivative thereof, to NAD+, or a derivative thereof; and
   (c) determining the amount of L-homocysteine and/or L-methionine in the original solution based on the amount of 2-ketobutyrate formed.

2. The method of claim 1, wherein the cofactor is pyridoxal phosphate or a derivative thereof.

3. The method of claim 2, wherein the pyridoxal phosphate, or derivative thereof, is present in the reagent in a concentration of from about 0.005 mM to about 1 mM.

4. The method of claim 1, wherein the solution is contacted with the reagent for a time sufficient to catalyze the reaction of L-homocysteine and/or L-methionine to form 2-ketobutyrate to substantial completion.

5. The method of claim 1, wherein the methionine gamma-lyase, or a derivative thereof, is present in the reagent in a concentration of from about 0.005 mg/ml to about 5 mg/ml.

6. The method of claim 1, wherein the reagent comprising methionine gamma-lyase further comprises NADH, or a derivative thereof, and lactic dehydrogenase or a derivative thereof.

7. The method of claim 1, wherein the total amount of oxidation of NADH, or derivative thereof, to NAD+, or derivative thereof, is determined by reacting the NAD+, or derivative thereof, with a dye capable of undergoing a color change when oxidized.

8. The method of claim 7, wherein the dye is selected from the group consisting of 2,6-dichlorophenolindophenol, tetrazolium compounds, phenazine methosulfate, methyl viologen, and derivatives thereof.

9. The method of claim 1, wherein the methionine gamma-lyase, or derivative thereof, and lactic dehydrogenase, or derivative thereof, are immobilized on a support material.

10. The method of claim 9, wherein the methionine gamma-lyase, or derivative thereof, lactic dehydrogenase, or derivative thereof, and NADH, or derivative thereof, are immobilized on a support material.

11. The method of claim 1, further comprising, prior to contacting the solution with the reagent, treating the solution with a reducing agent in a manner sufficient to reduce substantially all of any L-homocystine and mixed disulfides containing half homocystine that are present in the solution to produce L-homocysteine.

12. The method of claim 11, wherein the reducing agent is a borohydride salt or a thiol reducing agent.

13. The method of claim 11, wherein the reducing agent is a thiol reducing agent selected from the group consisting of β-mercaptoethanol, dithiothreitol, dithioerythritol, and thioacetic acid and salts thereof.

14. The method of claim 1, wherein the solution comprising L-homocysteine and/or L-methionine is a human biological fluid.

15. The method of claim 14, wherein the solution is blood or urine.

16. The method of claim 1, further comprising, prior to contacting the solution with the reagent, treating the solution with an agent capable of converting any pyruvate, 2-ketobutyrate and/or other 2-ketoacids present in the solution to compounds that will not react with the 2-ketobutyrate detecting agent.

17. The method of claim 16, wherein the converting agent is selected from the group consisting of borohydride reducing agents, lactic dehydrogenase in the presence of NADH, and 2,4-dinitrophenylhydrazine.

18. A method for the colorimetric detection of L-homocysteine and/or L-methionine in a sample comprising the steps of:
   (i) contacting a sample containing L-homocysteine and/or L-methionine with a solution, mixture, or support material comprising NADH, or a derivative thereof, lactic dehydrogenase, or a derivative thereof, methionine gamma-lyase, or a derivative thereof, a cofactor capable of forming a Schiff base with the L-methionine and/or L-homocysteine, and a dye capable of producing a color-change when oxidized; and (ii) determining the amount of L-homocysteine and/or L-methionine present based on the relative intensity of the observed color.

19. The method of claim 18, wherein the cofactor is pyridoxal phosphate or a derivative thereof.

20. The method of claim 19, wherein the pyridoxal phosphate, or derivative thereof, is present in the solution, in the mixture or on the support material in a concentration of from about 0.005 mM to about 1 mM.

21. The method of claim 18, wherein the dye is selected from the group consisting of 2,6-dichlorophenolindophenol, a tetrazolium compound, phenazine methosulfate, methyl viologen, and derivatives thereof.

22. The method of claim 18, wherein the NADH, or derivative thereof, lactic dehydrogenase, or derivative thereof, methionine gamma-lyase, or derivative thereof, cofactor, and dye capable of producing a color-change when oxidized are all immobilized on a support material.

23. The method of claim 22, wherein the support material is formed from at least one material selected from the group consisting of paper, filter paper, nylon, glass, ceramic, silica, alumina, diatomaceous earth, cellulose, Eupergit, polymethacrylate, polypropylene, polystyrene, polyethylene, polyvinylchloride, and derivatives thereof.

24. The method of claim 18, wherein the solution, mixture, or support material further comprises diaphorase.

25. The method of claim 22, wherein the support material further comprises diaphorase.

26. The method of claim 18, wherein the solution comprising L-homocysteine and/or L-methionine is a human biological fluid.

27. The method of claim 26, wherein the solution is blood or urine.

28. The method of claim 18, further comprising comparing the intensity of the color observed to those produced in a set of standard solutions of L-homocysteine and/or L-methionine.

29. The method of claim 18, further comprising, prior to contacting the sample with the solution, mixture, or support material, treating the sample with a reducing agent in a manner sufficient to reduce substantially all of any L-homocystine and mixed disulfides containing half homocystine that are present in the sample to produce L-homocysteine.

30. The method of claim 29, wherein the reducing agent is a borohydride salt or a thiol reducing agent.

31. The method of claim 29, wherein the reducing agent is a thiol reducing agent selected from the group consisting of β-mercaptoethanol, dithiothreitol, dithioerythritol, and thioacetic acid and salts thereof.

32. The method of claim 18, further comprising, prior to contacting the sample with the solution, mixture, or support material, treating the sample with an agent capable of converting any pyruvate, 2-ketobutyrate and/or other 2-ketoacids present in the sample to compounds that will not react with the 2-ketobutyrate detecting agent.

33. The method of claim 32, wherein the converting agent is selected from the group consisting of borohydride reducing agents, lactic dehydrogenase in the presence of NADH, and 2,4-dinitrophenylhydrazine.

34. A composition for measuring the amount of L-homocysteine and/or L-methionine in a solution, the composition comprising L-methionine gamma-lyase, or a derivative thereof, a cofactor capable of forming a Schiff base with the L-methionine and/or L-homocysteine, and at least one 2-ketobutyrate detecting agent, wherein the composition is substantially free of L-methionine, L-homocysteine, 2-ketobutyrate, pyruvate and mercury.

35. The composition of claim 34, wherein the composition contains less than 1% by weight, based on the total weight of the composition, L-methionine, L-homocysteine, 2-ketobutyrate, pyruvate and mercury.

36. The composition of claim 34, wherein the composition contains less than 0.5% by weight, based on the total weight of the composition, L-methionine, L-homocysteine, 2-ketobutyrate, pyruvate and mercury.

37. The composition of claim 34, wherein the cofactor is pyridoxal phosphate.

38. The composition of claim 34, further comprising NADH, or a derivative thereof, and lactic dehydrogenase, or a derivative thereof.

39. The composition of claim 38, further comprising a dye capable of undergoing a color change when oxidized.

40. The composition of claim 39, wherein the dye is selected from the group consisting of 2,6-dichlorophenolindophenol, a tetrazolium compound, phenazine methosulfate, methyl viologen, and derivatives thereof.

41. The composition of claim 34, further comprising diaphorase.

42. The composition of claim 34, further comprising 2,4-dinitrophenylhydrazine.

43. The composition of claim 34, further comprising a borohydride reducing agent or a thiol reducing agent.

44. A construction for measuring the amount of L-homocysteine and/or L-methionine in a solution, the construction comprising the composition of claim 36 associated with a support material.

45. The construction of claim 44, wherein the composition further comprises NADH, or a derivative thereof, and lactic dehydrogenase, or a derivative thereof.

46. The construction of claim 45, wherein the composition further comprises a dye capable of undergoing a color change when oxidized.

47. The construction of claim 46, wherein the composition further comprises diaphorase.

\* \* \* \* \*